United States Patent
Tseng

(10) Patent No.: US 6,506,162 B1
(45) Date of Patent: Jan. 14, 2003

(54) ELECTRONIC BLOOD PRESSURE GAUGE EQUIPPED WITH DISMOUNTABLE EXTERNAL MEMORY DEVICE

(75) Inventor: Daniel C. M. Tseng, Taipei Hsien (TW)

(73) Assignee: K-Jump Health Co., Ltd., Taipei Hsien (TW)

( * ) Notice: Subject to any disclaimer, the term of this patent is extended or adjusted under 35 U.S.C. 154(b) by 57 days.

(21) Appl. No.: 09/590,674

(22) Filed: Jun. 9, 2000

(51) Int. Cl.[7] ................................................. A61B 5/02
(52) U.S. Cl. ........................ 600/485; 600/481; 600/300; 128/900
(58) Field of Search .................... 600/481, 485–504, 600/300; 73/700, 756; 128/900, 897

(56) References Cited

U.S. PATENT DOCUMENTS

| | | | | |
|---|---|---|---|---|
| 4,995,399 A | * | 2/1991 | Hayashi et al. | 600/493 |
| 5,155,663 A | * | 10/1992 | Harase | 273/148 B |
| 5,566,676 A | * | 10/1996 | Rosenfeldt et al. | 600/485 |
| 5,735,286 A | * | 4/1998 | Notton et al. | 600/485 X |
| 5,827,179 A | * | 10/1998 | Lichter et al. | 600/300 |
| 6,120,456 A | * | 9/2000 | Oka et al. | 600/494 X |
| 6,159,147 A | * | 12/2000 | Lichter et al. | 600/300 |
| 6,241,679 B1 | * | 6/2001 | Curran | 600/485 |
| 6,251,080 B1 | * | 6/2001 | Henkin et al. | 600/500 X |

* cited by examiner

Primary Examiner—Kevin Shaver
Assistant Examiner—Navin Natnithithadha
(74) Attorney, Agent, or Firm—Bacon & Thomas

(57) ABSTRACT

An electronic blood pressure gauge equipped with dismountable external memory device includes a blood pressure gauge and a memory device with a reading section. After a user has plugged or placed his personal memory device in the reading section, the measured present data of blood pressure can be stored in the memory device so that the user can keep himself informed of his blood pressure from time to time.

4 Claims, 6 Drawing Sheets

ELECTRONIC BLOOD PRESSURE GAUGE EQUIPPED WITH DISMOUNTABLE EXTERNAL MEMORY DEVICE

BACKGROUND OF THE INVENTION

This invention relates generally to electronic blood pressure gauges, and more particularly, to an electronic blood pressure gauge equipped with a dismountable external memory device for memorizing a user's blood pressure data.

It is not unusual for many people to ignore their own health for one reason or another when struggling for a living in today's busy society. Unfortunately, it is occasionally a little late to remedy a problem by the time one is aware of red flags concerning one's health.

Take stroke for instance. The death rate is soaring year by year irrespective of age, at least in part because of overeating on the one hand and lack of sport on the other. However, strokes can be prevented by paying a little more attention to one's blood pressure in daily life and taking some necessary measures.

For keeping people informed of their blood pressure from time to time, personal electronic blood pressure gauges have been on the market for years. These gauges can measure a person's blood pressure and store the measured data in its internal memory, which is accessible for people to compare present data with previous personal data. However, memory capacity is limited and so is the stored personal blood pressure data, and thus the present data cannot help but overlap and eliminate previous data.

Some other kinds of memory are incapable of storing data when being fully loaded unless all the stored data is erased. In that case, a medicine doctor cannot trace a patient's blood pressure even when the patient carriers the electronic blood pressure gauge to the doctor.

SUMMARY OF THE INVENTION

The primary object of this invention is to provide an electronic blood pressure gauge equipped with dismountable external memory device, which is used to measure and store a user's blood pressure data each time so that the user may dismount the memory device and take it to his medicine doctor for tracing.

Another object of this invention is to provide a memory device for use by different people.

Yet another object of this invention is to provide a memory device that can store more data concerning blood pressure.

In order to realize the abovesaid objects, a memory reading section is arranged on an electronic blood pressure gauge for reading previous data after a user has plugged or placed his personal memory device in the reading section, so that after the present measurement is made, the related data will be added to the memory device so that the user can keep himself informed of his blood pressure from time to time.

For more detailed information regarding this invention together with further advantages or features thereof, at least an example of preferred embodiment will be elucidated below with reference to the annexed drawings.

BRIEF DESCRIPTION OF THE DRAWINGS

The related drawings in connection with the detailed description of this invention, which is to be made later, are described briefly as follows.

DETAILED DESCRIPTION OF THE PREFERRED EMBODIMENT

Figure 1B:
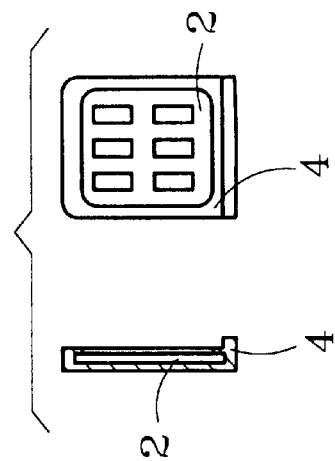
FIG. 1B is a schematic view of a memory device in FIG. 1A.
Figure 1A:
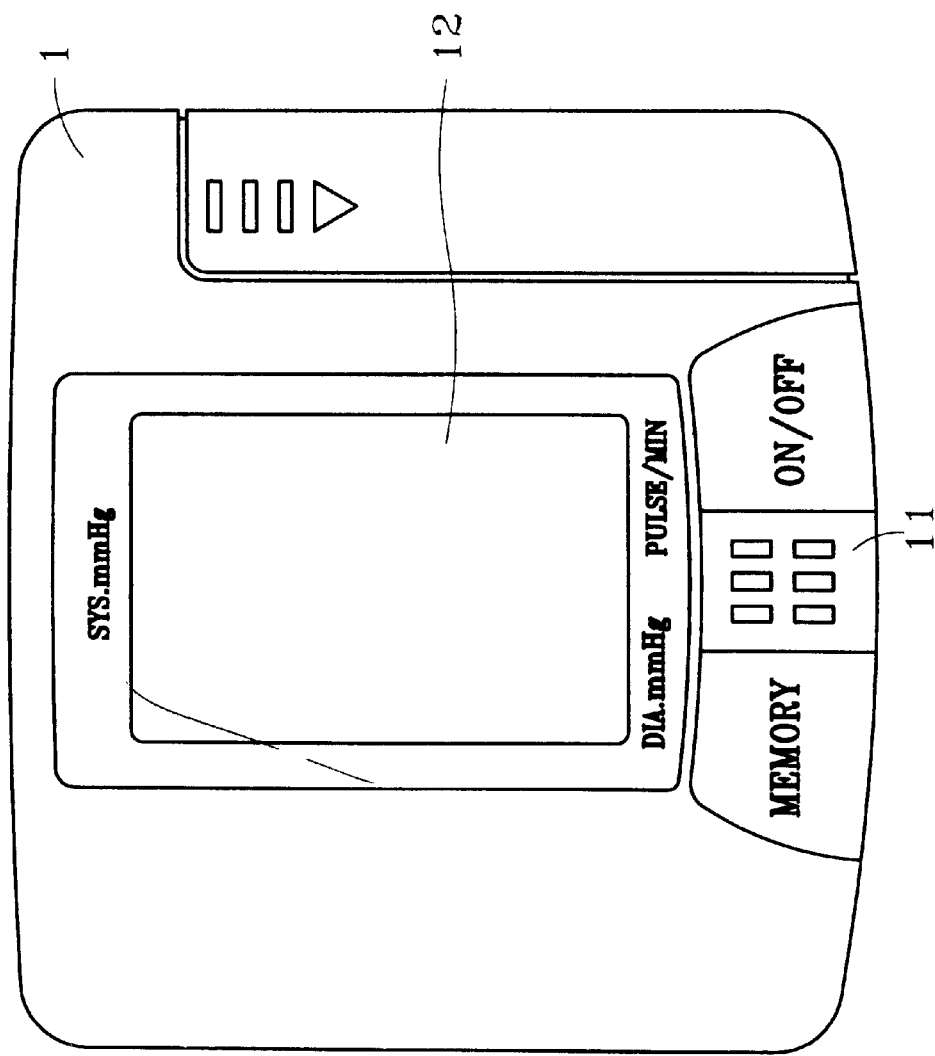
FIG. 1A illustrates a first embodiment of this invention.
Figure 2A:
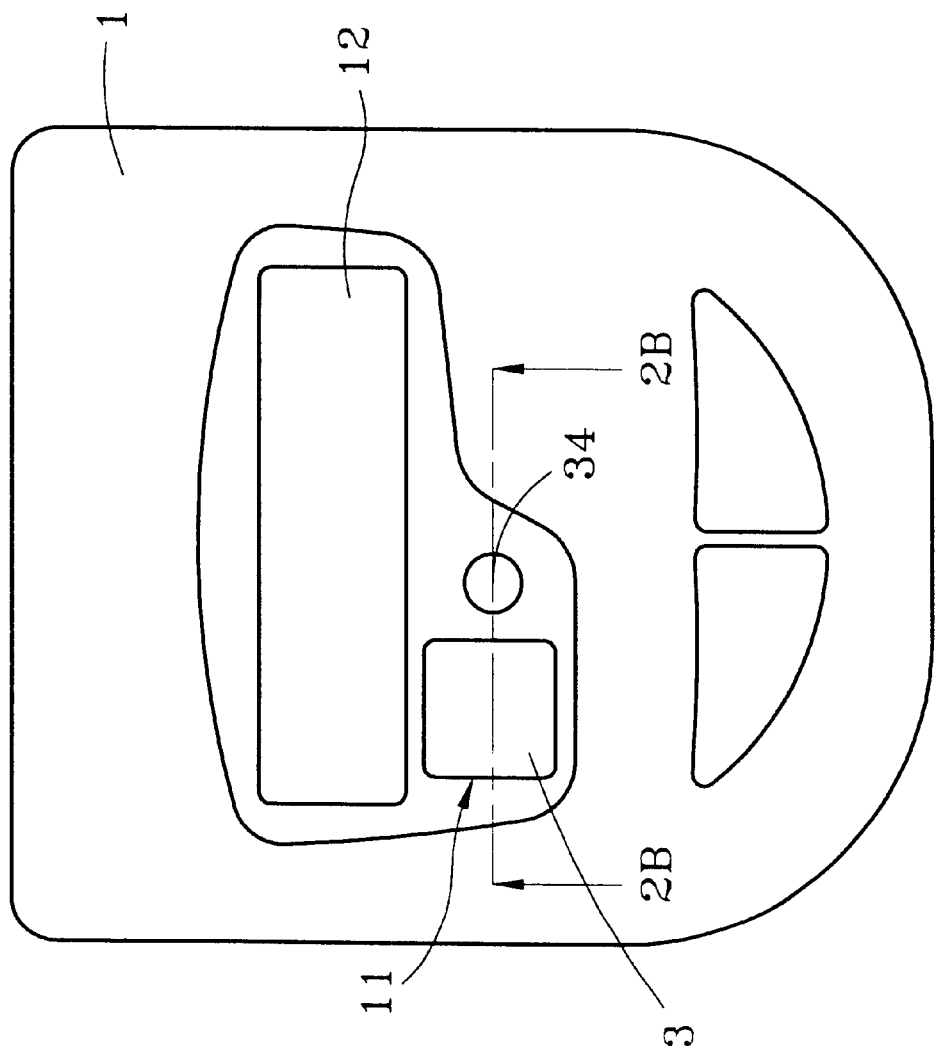
FIG. 2A illustrates a second embodiment of this invention.

An electronic blood pressure gauge equipped with a dismountable external memory constructed in accordance with the principles of this invention is shown in FIG. 1A and FIG. 2A. The device of this embodiment is provided with a memory device 2 arranged to be removably disposed on an electronic blood pressure gauge 1, wherein the memory device 2 may be, but is not limited to, a monolithic chip or a memory card. A reading section 11 is arranged on the blood pressure gauge 1 for reading the memory device 2. After the personal memory device 2 is plugged or placed in the reading section 11, the blood pressure gauge 1 can read and fetch the blood pressure data stored previously in the memory device 2, and after the present measurement is made, the new data will be stored in the memory device 2 as usual so that a user can keep himself informed of the blood pressure records of his own from time to time.

In a five-member family for example, each member may have his/her own memory card so that any member can plug or place his/her memory card in the reading section 11 of the blood pressure gauge 1 for measurement to build up an individual blood pressure record. A hypertension patient may take his/her memory card to a hospital and plug it in the reading section 11 of a hospital's blood pressure gauge 1 for the doctor to trace his/her clinic history and offer a proper cure.

In the first embodiment of this invention shown in FIG. 1A and FIG. 1B, the reading section 11 disposed on the blood pressure gauge 1 is designed to cooperate with a separate plug-in socket connector module structure. A user is requested to plug the memory device 2 in a jack 4, and then plug the jack 4 in the reading section 11. Internal circuits (a known technique not to be elucidated herein) of the blood pressure gauge 1 will read inside data of the memory device 2 and display it in a screen 12. The user may hook the memory device 2 with his or her fingers and extract it out of the reading section 11 after service of the blood pressure gauge 1.

Figure 2B:
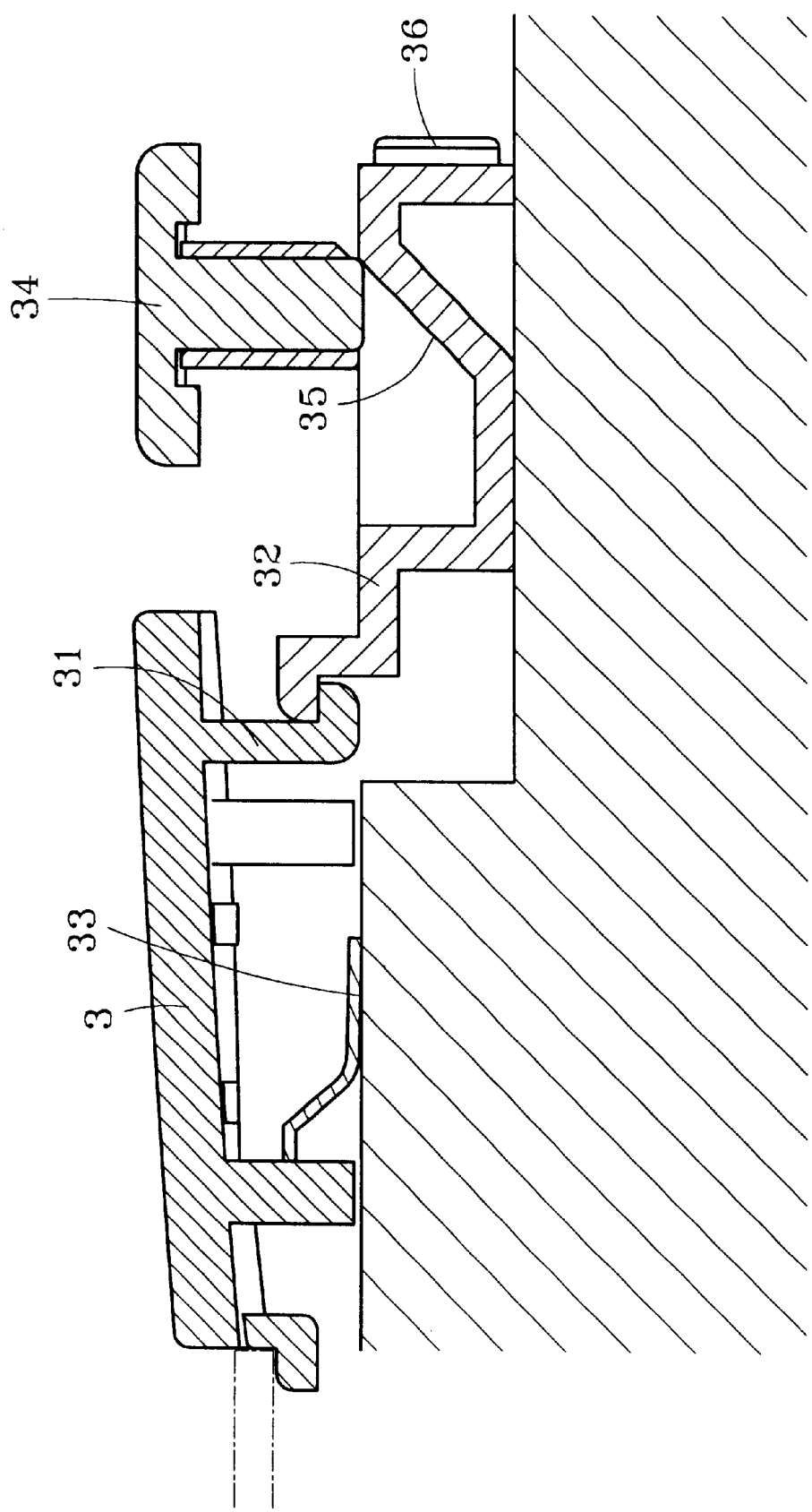
FIG. 2B is a cutaway sectional view taken along line 2B—2B in FIG. 2A.
Figure 2C:
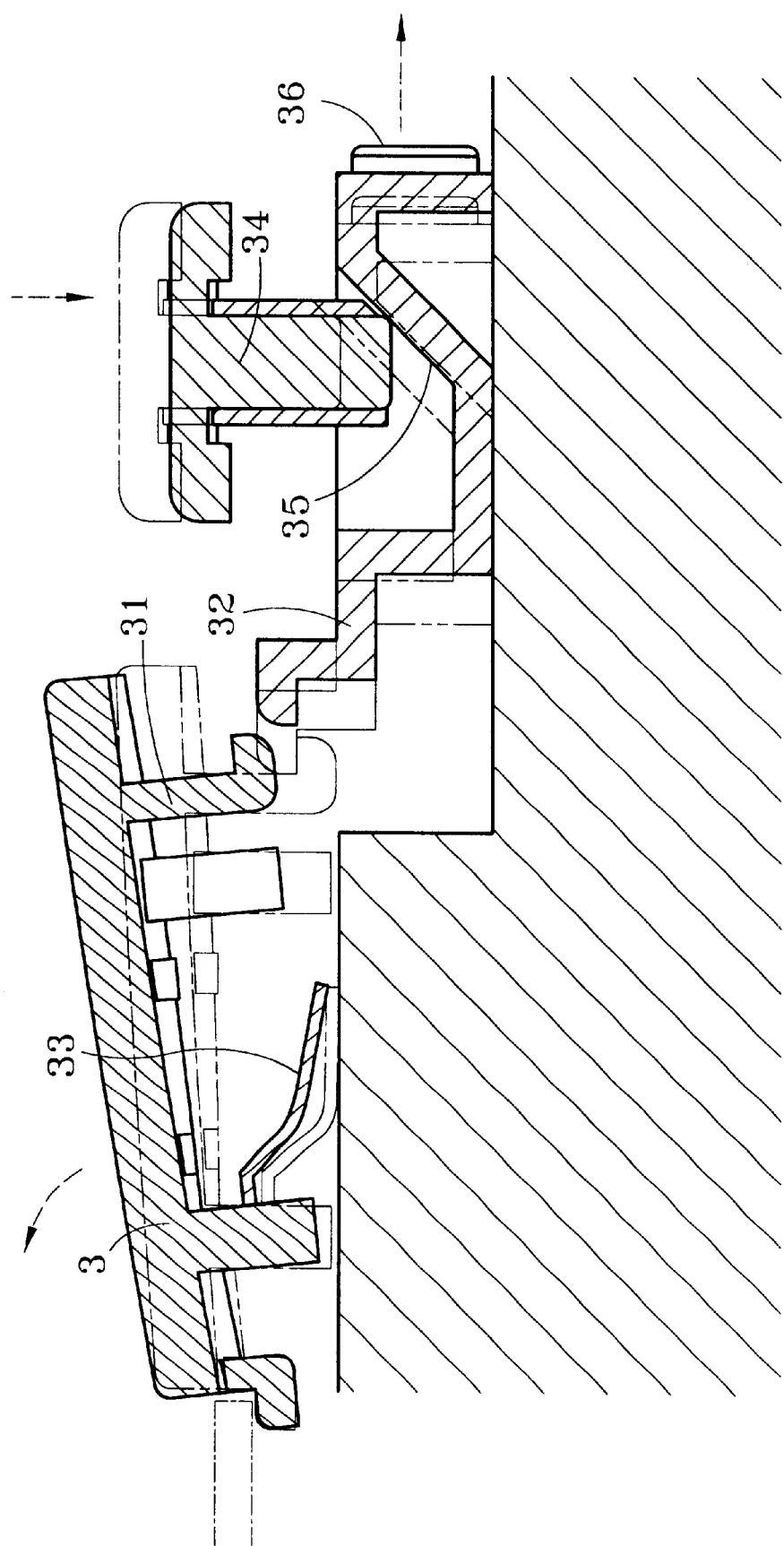
FIG. 2C illustrates an action mode of FIG. 2B.

In a second embodiment of this invention shown in FIGS. 2A, 2B, 2C, the reading section 11 disposed on the blood pressure gauge 1 is designed as a platform with an integral latch and connector structure. A user is requested to place the memory device 2 flat on a platform 3, then depress the platform 3 downwardly to enable a hook 31 at the bottom face of the platform 3 to engage with a snap-retainer 32. At this moment, a resilient member 33 molded integrally with the platform 3 is depressed and deformed to enable the blood pressure gauge 1 to read the data in the memory device 2 and display the data in the screen 12 of the blood pressure gauge 1.

After service of the blood pressure gauge 1, the user may depress a push-button 34 located laterally adjacent to the platform 3 to have the bottom end of the push-button 34 pressed against a slope 35 disposed laterally to the snap-retainer 32 and force the snap-retainer 32 to retreat to unbind the engagement relationship between the snap-retainer 32 and the hook 31. At this moment, no sooner has the hook 31 been freed, then the resilient member 33 restores and the platform 3 rebounds for the user to fetch the memory device 2. When the force is removed from the push-button 34, another resilient member 36 disposed at one end of the snap-retainer 32 will restore the snap-retainer 32.

Figure 3A:
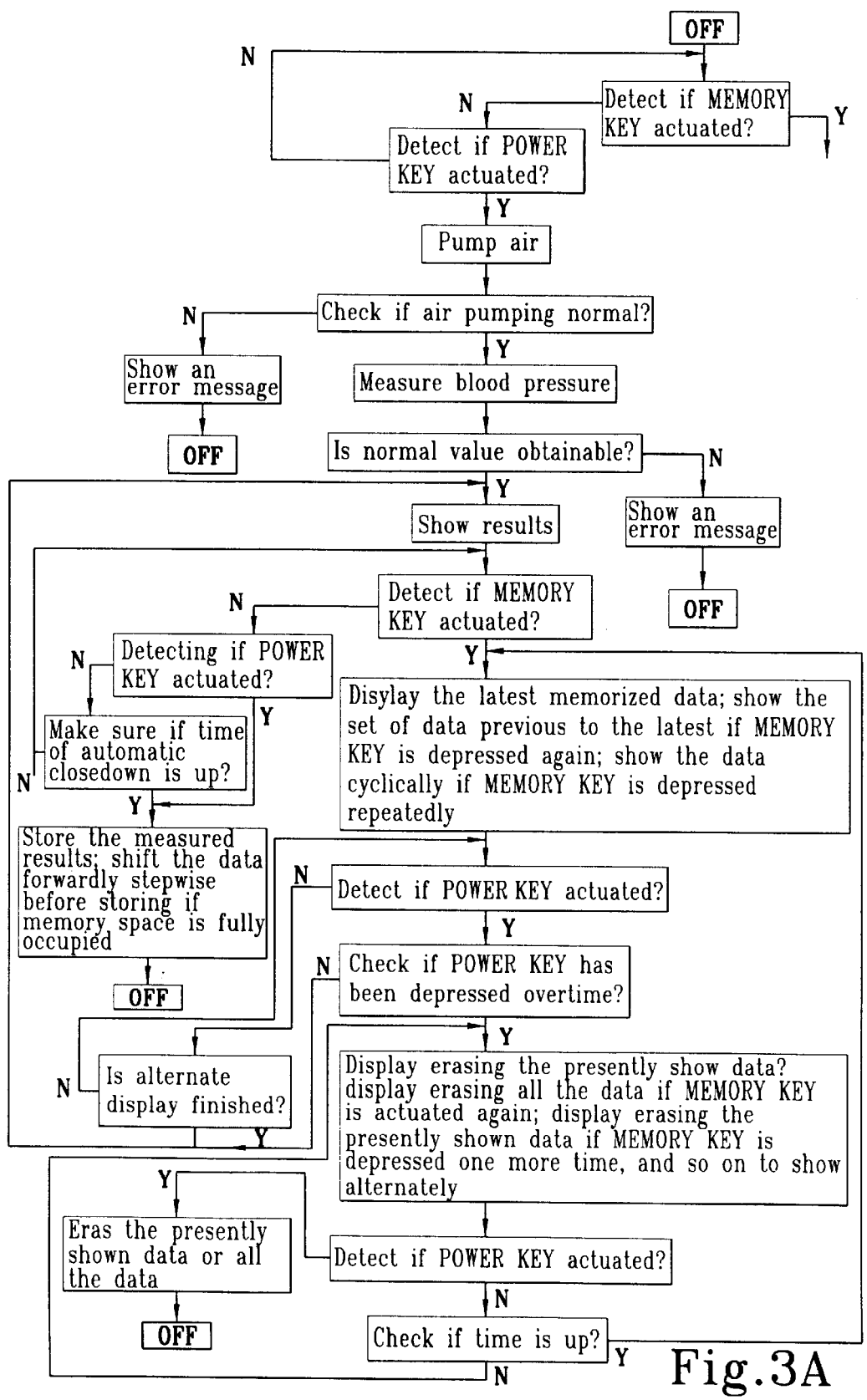
FIG. 3A is a flow chart illustrating blood pressure measurement of this invention.
Figure 3B:
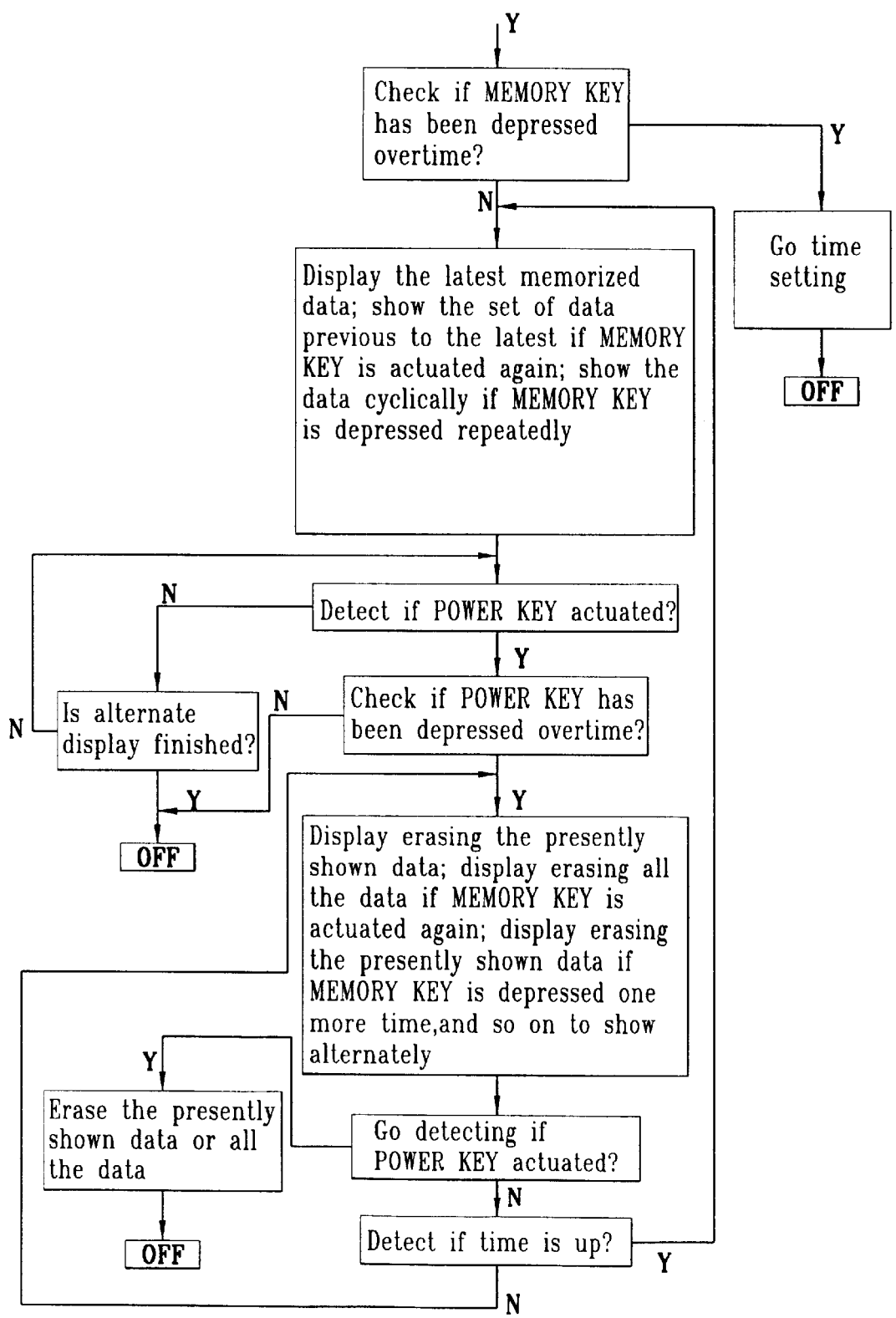
FIG. 3B is a partial chart of FIG. 3A.

As shown in FIGS. 3A, 3B, in measuring blood pressure, this inventions starts by detecting whether a MEMORY KEY is actuated (FIG. 3A); if YES, the invention proceeds to the steps shown in FIG. 3B, otherwise, the invention proceeds to the steps shown in FIG. 3A.

As shown in FIG. 3B the control program of the invention proceeds to detect whether the MEMORY KEY has been pressed overtime; if YES, the invention sets the time but if NO, the invention displays the latest memorized data. Then, the program detects whether the MEMORY KEY is actuated again; if YES, the memorized data previous to the latest data is displayed and so forth all the way to the first set data. If the MEMORY KEY is found actuated repeatedly, the program returns to the latest data and proceeds cyclically. The program also detects whether a POWER KEY is actuated. If NO, the program checks whether cyclic display is completed; if YES, it goes to the end or otherwise it returns to detect whether the POWER KEY is actuated; if YES, it erases the present set of data or all the data thus selected and goes to the end, otherwise, it checks whether time is over and, if NO, returns to display for selecting erasure of the present set of data, or otherwise goes on displaying the latest data.

According to the flowchart in FIG. 3A, the program detects whether a POWER KEY is actuated; if NO, it goes to the end, or otherwise it initiates pumping air. It then detects whether air is pumped normally; if NO, it shows an error message and goes to the end, otherwise the program enables measuring of blood pressure, detects whether a normal data is obtained and shows an error message if not, proceeding to the end, or otherwise, it shows the results. The program then detects whether the MEMORY KEY is actuated; if NO, it detects if the POWER KEY is actuated and, if NO again, makes sure whether time for an automatic closedown has elapsed. If the time has not elapsed, the program returns to detect whether the MEMORY KEY is actuated, otherwise, it stores the present data, and in case the memory space is used up, shifts the stored data one step forward before storing the present data, then goes to the end. If the POWER KEY is detected as being actuated, the program proceeds directly to store the present data, and in case the memory space is used up, shifts the stored data one step forward before storing the present data, then goes to the end. If the MEMORY KEY is found to be depressed, the program displays the latest data, but if the MEMORY KEY is found to be depressed one more time, the programs shows the set of data previous to the latest, such that the MEMORY KEY can be depressed repeatedly to show the inversely counted third set of data, the fourth . . . and so on, after which it again shows the latest set in a cyclical manner. The program then detects whether the POWER KEY is actuated; of NO, it detects whether the abovesaid data display is finished. If finished, the program shows the measured results, otherwise, it goes back to detecting whether the POWER KEY is actuated. If YES, the program checks whether the POWER KEY has been depressed overtime. If it has not been depressed overtime, the program shows the measured data. Otherwise, it displays an erasure message for the presently shown data. If the MEMORY KEY is depressed again, it indicates that all the data will be erased, and if one more time the MEMORY KEY is actuated, returns to the indication that only the presently shown data will be erased, and so forth. The program then detects whether the POWER KEY is actuated; if YES, it erases the present data or all the data depending on the selection and goes to the end. Otherwise, the program detects whether time is up. If NO, it returns to the display indicating erasure of the shown data, or otherwise goes on displaying the latest data.

Although, this invention has been described in terms of preferred embodiments, it is apparent that numerous variations and modifications may be made without departing from the true spirit and scope thereof, as set forth in the following claims.

What is claimed is:

1. An electronic blood pressure gauge equipped with a dismountable external memory device, comprising:

an electronic blood pressure gauge having a reading section; and a memory device arranged to be plugged or placed in the reading section for storing presently and previously measured blood pressure data, which can be fetched and displayed, wherein said electronic blood pressure gauge includes a snap-retainer and a platform situated at said reading section and arranged to receive said memory device, said platform including an integrally-molded hook and said snap-retainer including a slope disposed laterally of the snap-retainer; and said electronic pressure gauge further including a first resilient member disposed at a bottom face of the platform, a push-button situated above the slope, and a second resilient member arranged at one end of the snap-retainer, wherein said snap-retainer being arranged to engage said hook when said platform is pressed against a restoring force of said first resilient member to latch said platform and memory device in a reading position in which said presently and previously measure blood pressure data can be fetched and displayed, and wherein said button is arranged to engage said slope when depressed to cause said snap-retainer to move against a restoring force of said second resilient member and thereby unlatch said platform.

2. The electronic blood pressure gauge equipped with a dismountable external memory device according to claim 1, wherein the memory device is a monolithic chip.

3. The electronic blood pressure gauge equipped with a dismountable external memory according to claim 1, wherein the memory device is a memory card.

4. An electronic blood pressure gauge equipped with a dismountable external memory, comprising:

an electronic blood pressure gauge having a reading section;

a jack; and a memory device arranged to store presently and previously measured blood pressure data, wherein the memory device is arranged to be plugged into the jack, and wherein the jack is arranged to be plugged into the reading section of the electronic blood pressure gauge to enable the presently and previously measured blood pressure data to be fetched from the memory device and displayed by the electronic blood pressure gauge, wherein the memory device is a monolithic chip.

* * * * *